United States Patent
Takeda et al.

(10) Patent No.: US 9,109,297 B2
(45) Date of Patent: Aug. 18, 2015

(54) METHOD FOR PRODUCTION OF ACCUMULATED PRODUCT OF NANO-SUBSTANCE, ACCUMULATED PRODUCT OF NANO-SUBSTANCE, DEVICE COMPRISING THE ACCUMULATED PRODUCT, AND METHOD FOR ANALYSIS OF STRUCTURE OF NANO-SUBSTANCE

(75) Inventors: Yoshihiro Takeda, Urayasu (JP); Fumitaka Mafune, Tokyo (JP); Tamotsu Kondow, Chiba (JP); Kazuko Kondow, legal representative, Chiba (JP)

(73) Assignees: GENESIS RESEARCH INSTITUTE, INCORPORATED (JP); THE UNIVERSITY OF TOKYO (JP)

( * ) Notice: Subject to any disclaimer, the term of this patent is extended or adjusted under 35 U.S.C. 154(b) by 475 days.

(21) Appl. No.: 13/386,207

(22) PCT Filed: Jul. 30, 2010

(86) PCT No.: PCT/JP2010/063341
§ 371 (c)(1),
(2), (4) Date: Feb. 14, 2012

(87) PCT Pub. No.: WO2011/013857
PCT Pub. Date: Feb. 3, 2011

(65) Prior Publication Data
US 2012/0135439 A1    May 31, 2012

(30) Foreign Application Priority Data
Jul. 31, 2009    (JP) .................................. 2009-179345

(51) Int. Cl.
C30B 7/00    (2006.01)
C07K 1/30    (2006.01)
C30B 29/58    (2006.01)

(52) U.S. Cl.
CPC . *C30B 7/00* (2013.01); *C07K 1/306* (2013.01); *C30B 29/58* (2013.01)

(58) Field of Classification Search
None
See application file for complete search history.

(56) References Cited

U.S. PATENT DOCUMENTS 4,795,698 A * 1/1989 Owen et al. ....................... 435/4
5,139,611 A   8/1992 Pusey et al.
5,437,892 A   8/1995 Nagayama et al.
5,837,333 A  11/1998 Nagayama et al.
2002/0015792 A1  2/2002 Nagayama et al.
2004/0142164 A1  7/2004 Yamashita

FOREIGN PATENT DOCUMENTS

| JP | 6-279199 A | 10/1994 |
| JP | 7-116502 A | 5/1995 |
| JP | 2693844 B2 | 9/1997 |
| JP | 2905712 B2 | 3/1999 |
| JP | 2003-342605 A | 12/2003 |
| JP | 2004-226891 A | 8/2004 |
| JP | 2004-240008 A | 8/2004 |
| JP | 2005-224653 A | 8/2005 |
| JP | 2007-147285 A | 6/2007 |
| WO | 03/040025 A1 | 5/2003 |

OTHER PUBLICATIONS

Hideyuki Yoshimura, "Protein-assisted nanoparticle synthesis", Department of Physics, Meiji University, Japan, Colloids and Surfaces A, Jul. 20, 2006, Physicochem. Eng. Aspects 282-283, pp. 464-470.
Yoshitake Masuda, "Self-Assembly Patterning of Nanoparticles and Their Novel Functions", Materials Science and Technology, 2006, vol. 76(3), pp. 284-292 (32-40).
Satoshi Abe et al., "Metal Accumulation on the Surface of Porous Protein Crystal", iCeMs, Kyoto Univ., published Mar. 13, 2009, vol. 89th, No. 2, p. 1259 (3 H5-46), Abstract in English.
Yoshihiro Takeda et al., "Assembly of Gold Nanoparticles in Lysozyme Crystal", Genesis Research Institute, Inc., the University of Tokyo, Toyota Technological Institute, published Mar. 12, 2010, vol. 90th, No. 3, p. 670 (1 C3-55).
Tomokazu Matsue et al., "Rapid micropatterning of living cells by repulsive dielectrophoretic force", Department of Applied Chemistry, Graduate School of Engineering and Center for Interdisciplinary Research, Tohoku University, Sendai Japan, revised from Jan. 6, 1997, Electrochimica Acta, vol. 42, Nos. 20-22, pp. 3251-3256.
International Search Report for International Application No. PCT/JP2010/063341, mailed Sep. 14, 2010, with English translation.

* cited by examiner

*Primary Examiner* — Anand Desai
(74) *Attorney, Agent, or Firm* — Cantor Colburn LLP

(57) ABSTRACT

A method for producing an accumulated product of a nano-substance that enables the accumulated product of the nano-substance to be produced at low cost, by a simple process that requires few conditions to be controlled and requires minimal energy, and with good reproducibility. Specifically, a method for producing an accumulated product of a nano-substance, the method including crystallizing a protein in a state where the protein and the nano-substance co-exist within a solvent, thereby accumulating the nano-substance within pores of the protein crystals to obtain the accumulated product of the nano-substance.

16 Claims, 12 Drawing Sheets

METAL MICROPARTICLE

METAL MICROPARTICLE

METAL MICROPARTICLE

METAL MICROPARTICLE

METAL MICROPARTICLE

METHOD FOR PRODUCTION OF ACCUMULATED PRODUCT OF NANO-SUBSTANCE, ACCUMULATED PRODUCT OF NANO-SUBSTANCE, DEVICE COMPRISING THE ACCUMULATED PRODUCT, AND METHOD FOR ANALYSIS OF STRUCTURE OF NANO-SUBSTANCE

CROSS REFERENCE TO RELATED APPLICATIONS

This is a U.S. national stage of application No. PCT/JP2010/063341, filed on Jul. 30, 2010. Priority under 35 U.S.C. §119(a) and 35 U.S.C. §365(b) is claimed from Japanese Application No. 2009-179345, filed Jul. 31, 2009, the disclosure of which is also incorporated herein by reference.

TECHNICAL FIELD

The present invention relates to a method for producing an accumulated product of a nano-substance (nanomaterial), an accumulated product of a nano-substance and a device comprising the accumulated product, and a method for analyzing the structure of a nano-substance using the accumulated product of the nano-substance.

BACKGROUND ART

Accumulated products of nano-substances such as microparticles exhibit properties that are not observed in bulk materials, and therefore much research is currently being conducted into the multidimensional ordering of microparticles with the anticipation of generating novel devices. In particular, research and development into the use of three dimensional accumulated products of microparticles as photonic crystals is thriving. Photonic crystals are substances which utilize the appearance of forbidden wavelengths, where light of specific wavelengths disappears due to refraction or diffraction or the like, within the interior of substances in which the refractive index varies periodically with a length (distance between the microparticles that form the crystal lattice) that is substantially equivalent to the wavelength of light, and have been so named because the appearance of these forbidden wavelengths is very similar to the formation of forbidden electron transition bands in semiconductor crystals.

Examples of known techniques relating to the production of accumulated products of nano-substances such as microparticles include those listed below.

(1) A method that includes incorporating a gelling agent within a microparticle solution, gelling the mixture once the microparticles have adopted a three dimensional ordered structure, and fixing the three dimensional ordered structure of microparticles within a matrix (see Patent Document 1).

(2) A method of accumulating the particles by gravity.

(3) A method that utilizes the forces of an electric field within a liquid (see Non-Patent Document 1).

(4) A method of forming an ordered structure by utilizing the repulsive forces between the surfaces of microparticles (see Patent Document 2).

(5) A method of forming a microparticle thin film, which is related to the method of ordering microparticles by utilizing the repulsive forces between the surfaces of microparticles, and includes dispersing microparticles within a medium comprising two or more liquid mixtures having different values of vapor pressure and surface tension between microparticles, and flow casting the resulting microparticle dispersion onto the surface of a substrate to form a lattice-ordered liquid film (see Patent Document 3).

(6) A method of dipping a substrate in a microparticle suspension, and then drawing the substrate out of the suspension to form a microparticle monolayer film by advection accumulation.

(7) A method of obtaining a microparticle accumulated product by inserting a microparticle solution within a comparatively narrow space between parallel surfaces, and then using a stepping motor and a linear translation device to subject the solution to oscillation at a frequency greater than the Brownian motion of the microparticles and at an amplitude approximately equal to the spacing between the two parallel surfaces (see Patent Document 4).

(8) A method that uses a self-assembled monolayer as a template for selectively ordering microparticles. In this method, by using a self-assembled monolayer (SAM) formed on a substrate as a template, and utilizing the hydrophilicity, hydrophobicity, chemical reactivity, zeta potential, molecular recognition ability or the like of the functional groups at the SAM surface, precise ordering of microparticles can be achieved (see Non-Patent Document 2).

CITATION LIST

Patent Documents

Patent Document 1: JP 2004-226891 A
Patent Document 2: JP 07-116502 A
Patent Document 3: JP 2,905,712 B
Patent Document 4: JP 2,693,844 B Non-Patent Documents Non-Patent Document 1: T. Matsue, N. Matsumoto and I. Uchida, Electrochimica Acta, vol. 42, pp. 3251 to 3256 (1997).
Non-Patent Document 2: Yoshitake Masuda, Kinzoku (Metals), vol. 76, pp. 284 to 292 (2006).

SUMMARY OF INVENTION

Technical Problems

As described above, in conventional techniques used for obtaining accumulated products of nano-substances such as microparticles, impractically long periods of time are necessary, the systems and processes required are unavoidably complex, the number of conditions that must be controlled is large, and reproducibility and controllability have proven to be significant problems. Further, in order to control the refractive index, the dielectric constant and the magnetic susceptibility of photonic materials, accumulation techniques must be able to be applied to microparticles including materials that combine a high refractive index with a high dielectric constant, such as semiconductor crystals and transition metals and the like, and microparticles having a variety of different particle sizes. Accordingly, the accumulation of nano-substances such as microparticles is still faced with many problems, and resolutions to these problems are currently being sought.

The present invention provides a method for producing an accumulated product of a nano-substance that enables the accumulated product of the nano-substance to be produced at low cost, by a simple process that requires few conditions to be controlled and requires minimal energy, and with good reproducibility, as well as providing an accumulated product of a nano-substance and a device comprising the accumulated product, and a method for analyzing the structure of a nano-substance using the accumulated product of the nano-substance.

Solution to the Problems

The present invention provides a method for producing an accumulated product of a nano-substance, the method comprising crystallizing a protein in a state where the protein and the nano-substance co-exist within a solvent, thereby accumulating the nano-substance within pores of the protein crystals to obtain the accumulated product of the nano-substance.

Further, in the above method for producing an accumulated product of a nano-substance, a protein solubility regulator that regulates the solubility of the protein preferably also co-exists within the solvent.

Furthermore, in the above method for producing an accumulated product of a nano-substance, the nano-substance is preferably at least one of a metal microparticle and a biomolecule.

Further, the present invention also provides an accumulated product of a nano-substance which is obtained using a method for producing the accumulated product of the nano-substance that comprises crystallizing a protein in a state where the protein and the nano-substance co-exist within a solvent, thereby accumulating the nano-substance within pores of the protein crystals to obtain the accumulated product of the nano-substance.

Furthermore, the present invention also provides a device that uses an accumulated product of a nano-substance, the device comprising an accumulated product of a nano-substance which is obtained using a method for producing the accumulated product of the nano-substance that comprises crystallizing a protein in a state where the protein and the nano-substance co-exist within a solvent, thereby accumulating the nano-substance within pores of the protein crystals to obtain the accumulated product of the nano-substance.

Moreover, the present invention also provides a method for analyzing the structure of a nano-substance, the method using an accumulated product of the nano-substance which is obtained using a method for producing the accumulated product of the nano-substance that comprises crystallizing a protein in a state where the protein and the nano-substance co-exist within a solvent, thereby accumulating the nano-substance within pores of the protein crystals to obtain the accumulated product of the nano-substance.

Advantageous Effects of the Invention

The present invention provides a method for producing an accumulated product of a nano-substance that enables the accumulated product of the nano-substance to be produced at low cost, by a simple process that requires few conditions to be controlled and requires minimal energy, and with good reproducibility.

Further, it is thought that using accumulated products of nano-substances produced in this manner will lead to the development of novel devices that employ combinations of proteins and nano-substances.

Furthermore, it is also thought that using accumulated products of nano-substances produced in this manner will enable the development of novel methods of analyzing the structures of nano-substances.

Figure 1:
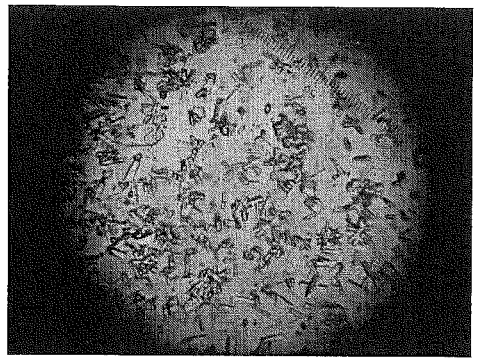
FIG. 1 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, and a pH 3 buffer concentration of 100 mM.
Figure 2:
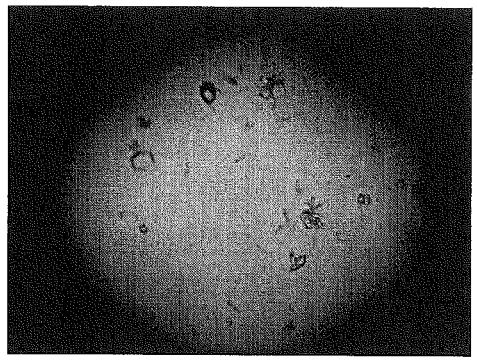
FIG. 2 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, and a pH 4 buffer concentration of 100 mM.
Figure 3:
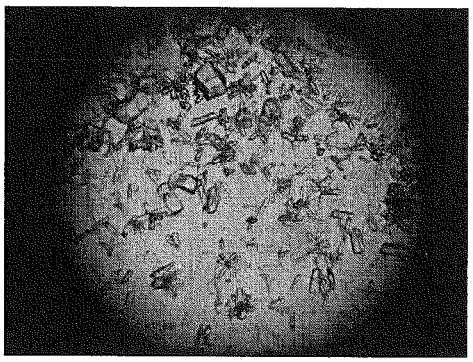
FIG. 3 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, and a pH 5 buffer concentration of 100 mM.
Figure 4:
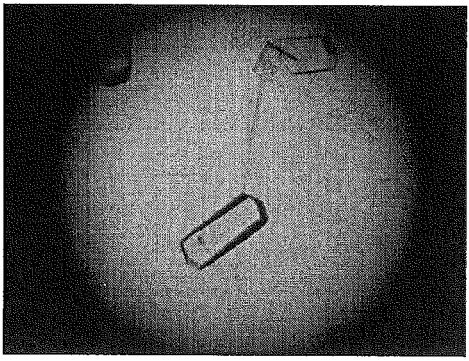
FIG. 4 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, and a pH 6 buffer concentration of 100 mM.
Figure 5:
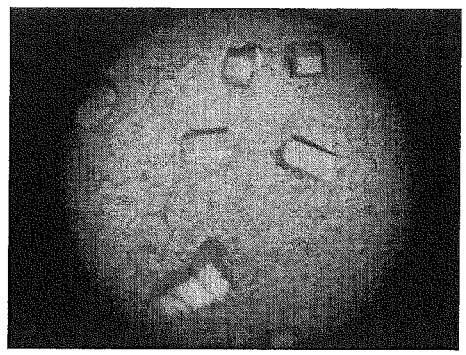
FIG. 5 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, and a pH 7 buffer concentration of 100 mM.
Figure 6:
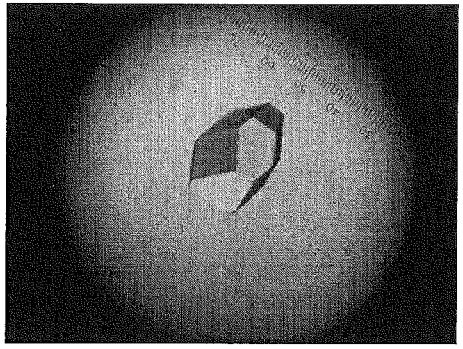
FIG. 6 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, and a pH 8 buffer concentration of 100 mM.
Figure 7:
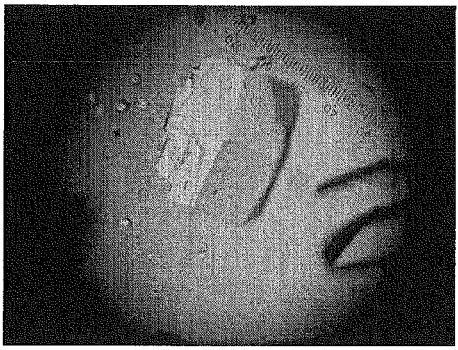
FIG. 7 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, and a pH 9 buffer concentration of 100 mM.
Figure 8:
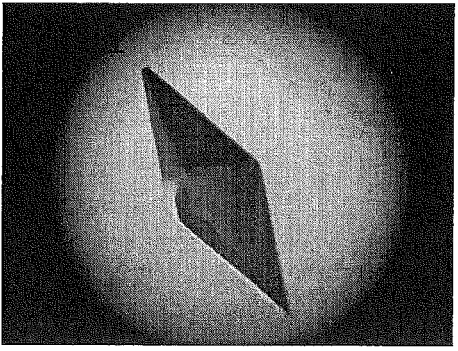
FIG. 8 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, and a pH 11 buffer concentration of 100 mM.
Figure 9:
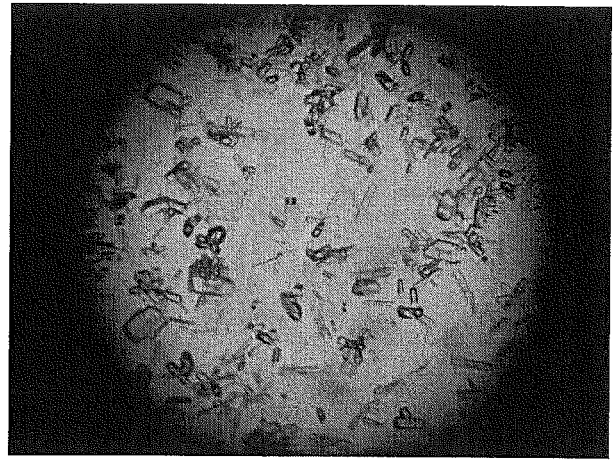
FIG. 9 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 3 buffer concentration of 100 mM, and also containing gold microparticles.
Figure 10:
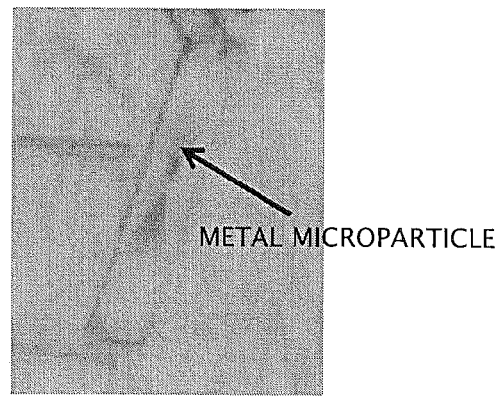
FIG. 10 is an enlarged view of a crystal portion from FIG. 9.
Figure 11:
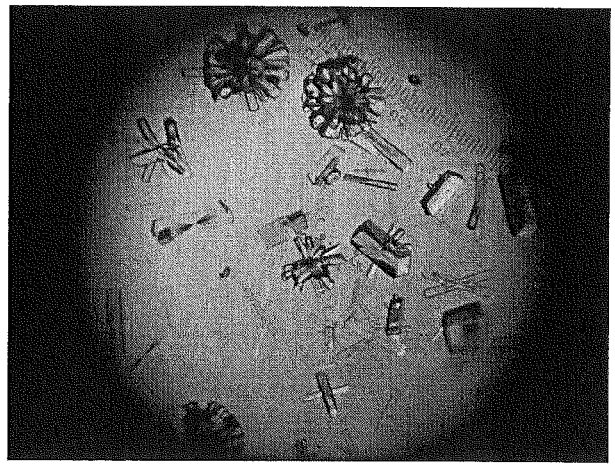
FIG. 11 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 4 buffer concentration of 100 mM, and also containing gold microparticles.
Figure 12:
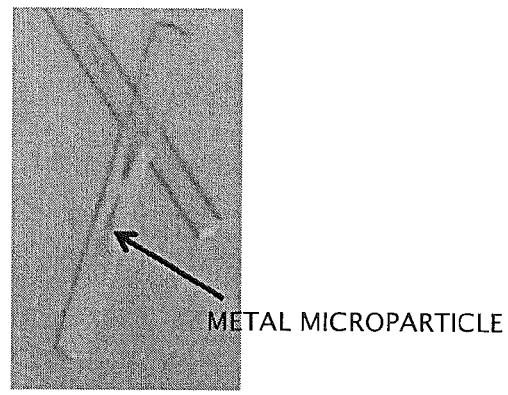
FIG. 12 is an enlarged view of a crystal portion from FIG. 11.
Figure 13:
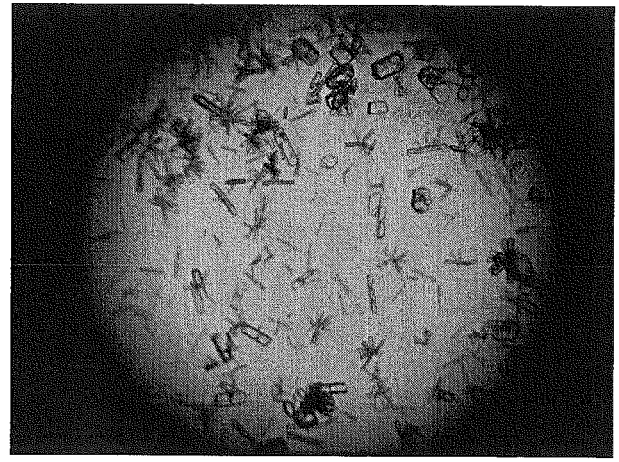
FIG. 13 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 5 buffer concentration of 100 mM, and also containing gold microparticles.
Figure 14:
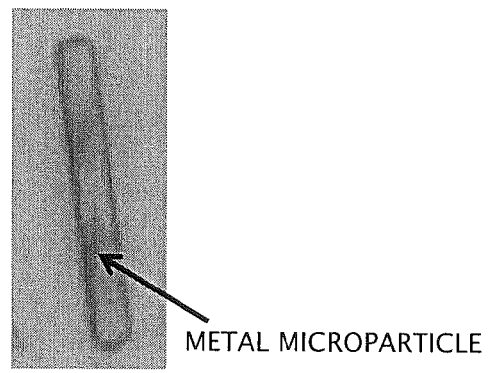

FIG. 14 is an enlarged view of a crystal portion from FIG. 13.

Figure 15:
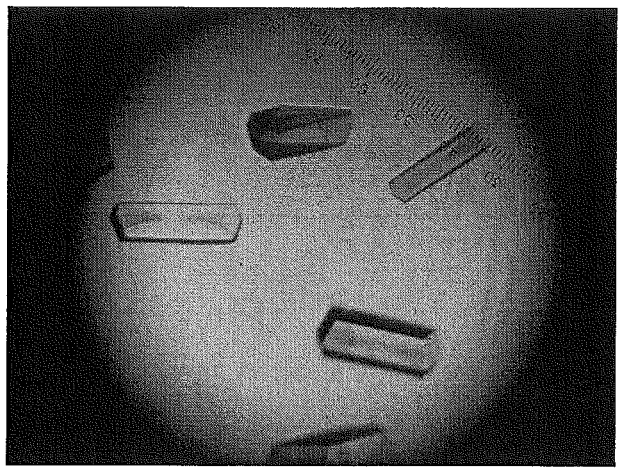

FIG. 15 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 6 buffer concentration of 100 mM, and also containing gold microparticles.

Figure 16:
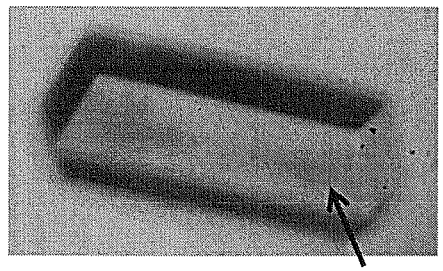

FIG. 16 is an enlarged view of a crystal portion from FIG. 15.

Figure 17:
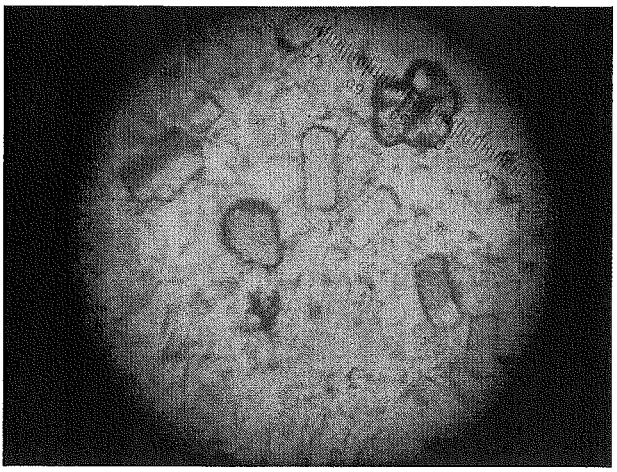

FIG. 17 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 7 buffer concentration of 100 mM, and also containing gold microparticles.

Figure 18:
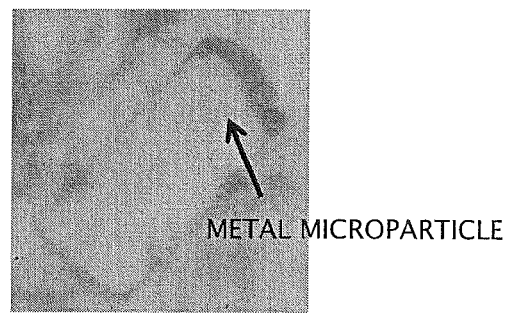

FIG. 18 is an enlarged view of a crystal portion from FIG. 17.

Figure 19:
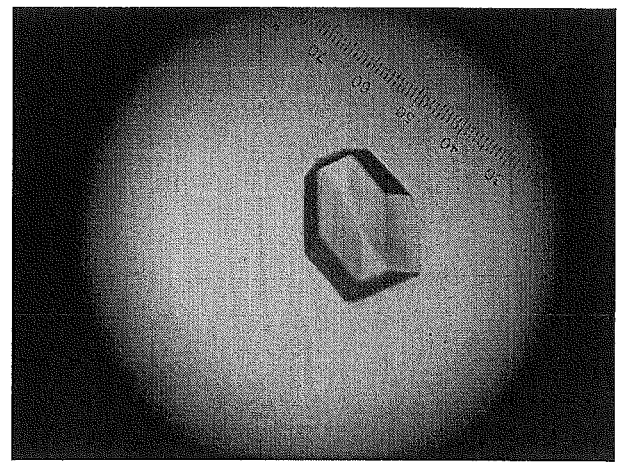

FIG. 19 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 8 buffer concentration of 100 mM, and also containing gold microparticles.

Figure 20:
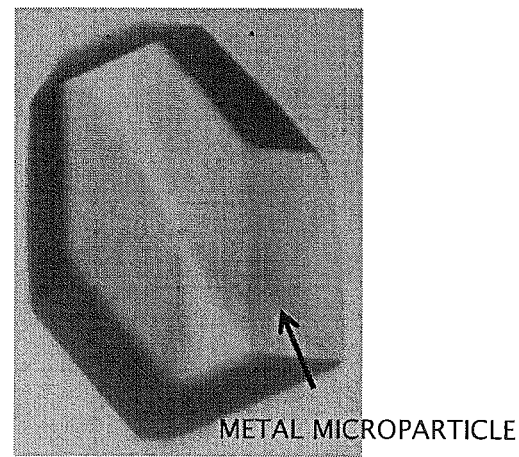

FIG. 20 is an enlarged view of a crystal portion from FIG. 19.

Figure 21:
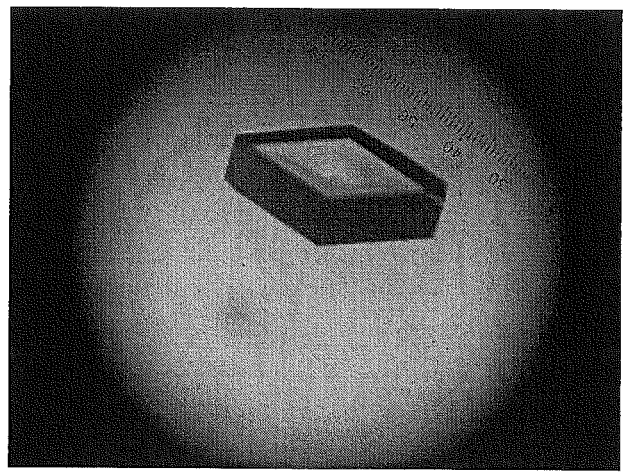

FIG. 21 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 9 buffer concentration of 100 mM, and also containing gold microparticles.

Figure 22:
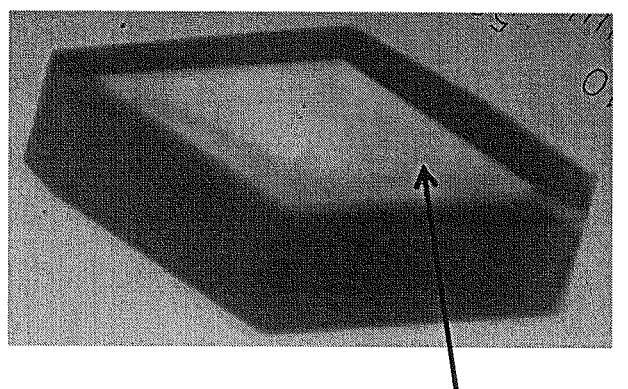

FIG. 22 is an enlarged view of a crystal portion from FIG. 21.

Figure 23:
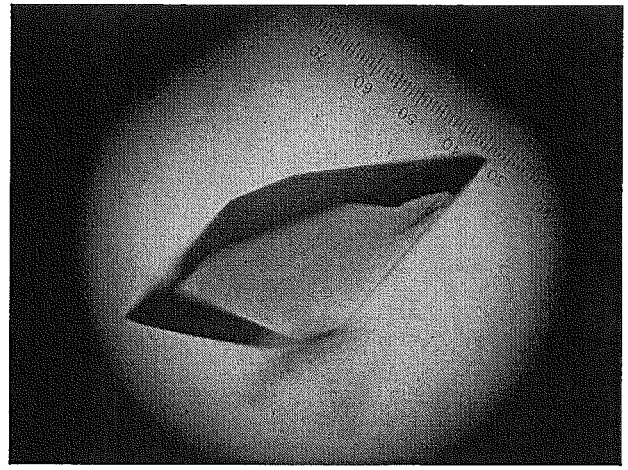

FIG. 23 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 11 buffer concentration of 100 mM, and also containing gold microparticles.

Figure 24:
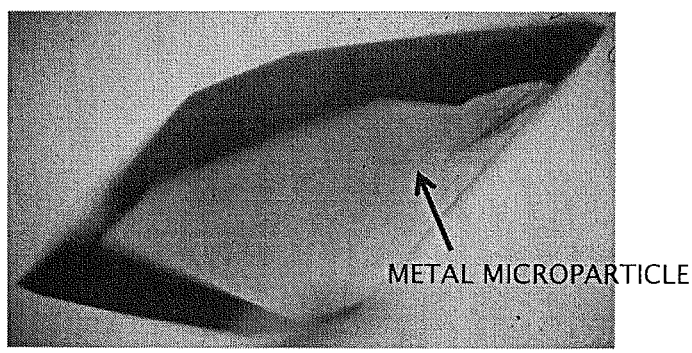

FIG. 24 is an enlarged view of a crystal portion from FIG. 23.

Figure 25:
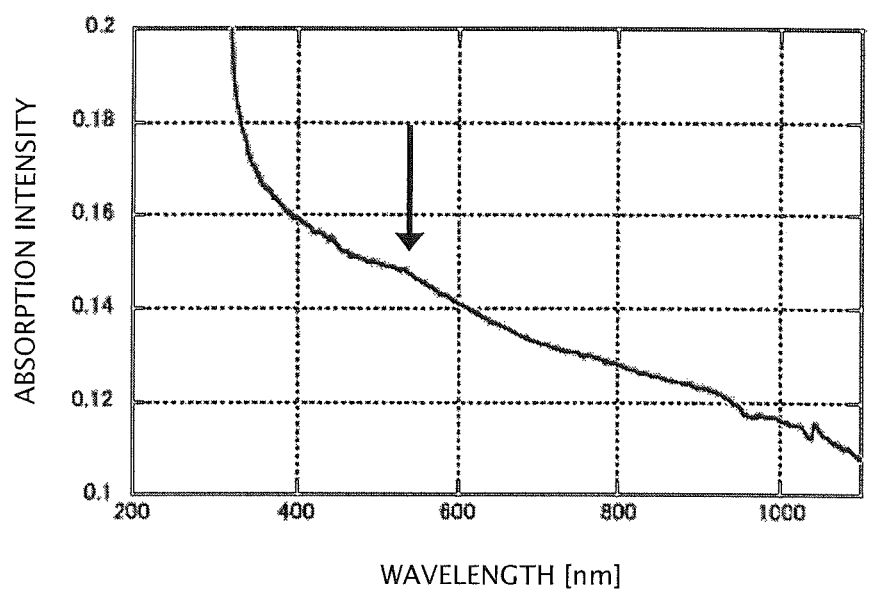

FIG. 25 is a diagram illustrating the ultraviolet-visible spectrum of lysozyme crystals containing multidimensionally accumulated gold microparticles. The arrow indicates the position of surface plasmon resonance of the gold microparticles.

Figure 26:
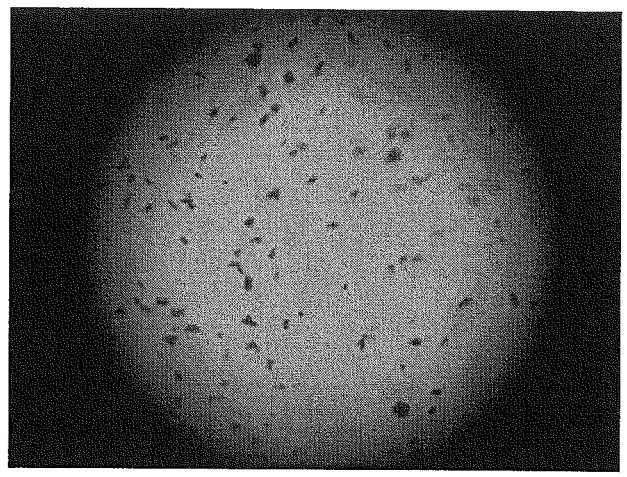

FIG. 26 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 7 buffer concentration of 100 mM, and also containing silver microparticles.

Figure 27:
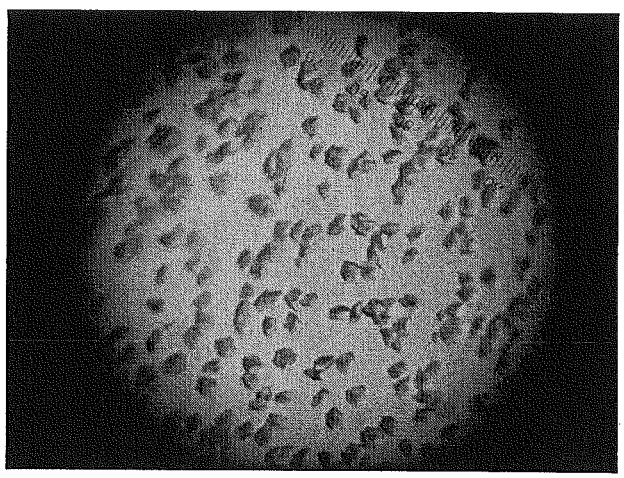

FIG. 27 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 8 buffer concentration of 100 mM, and also containing silver microparticles.

Figure 28:
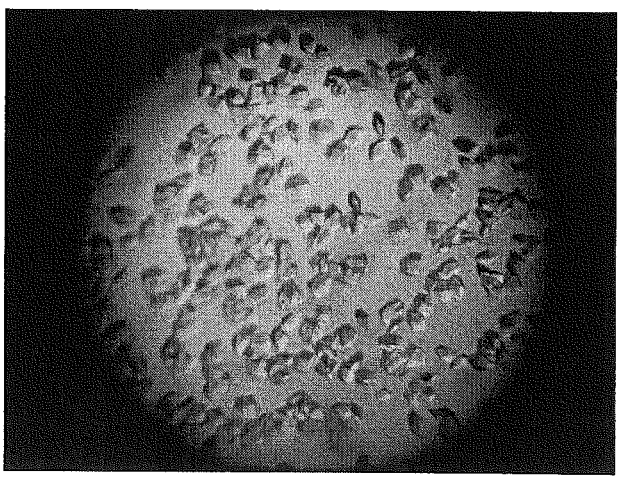

FIG. 28 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 9 buffer concentration of 100 mM, and also containing silver microparticles.

Figure 29:
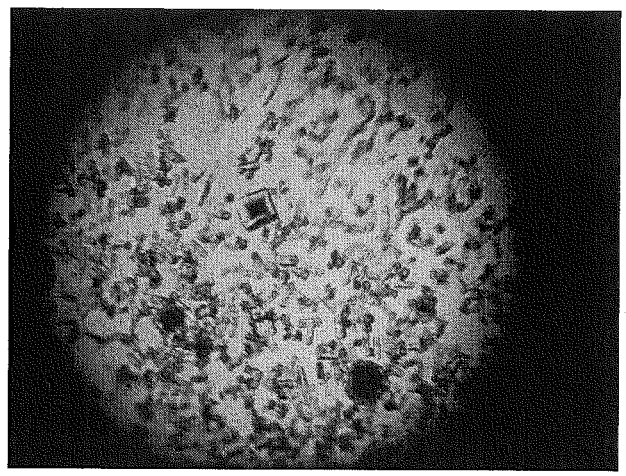

FIG. 29 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 6 buffer concentration of 100 mM, and also containing platinum microparticles.

Figure 30:
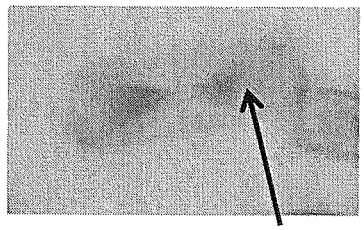

FIG. 30 is an enlarged view of a crystal portion from FIG. 29.

Figure 31:
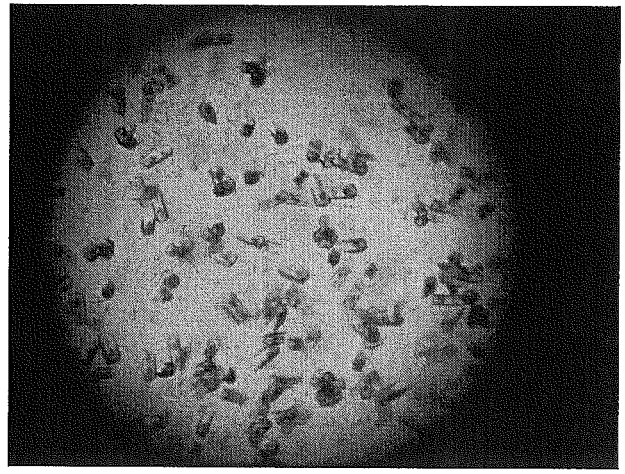

FIG. 31 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 7 buffer concentration of 100 mM, and also containing platinum microparticles.

Figure 32:
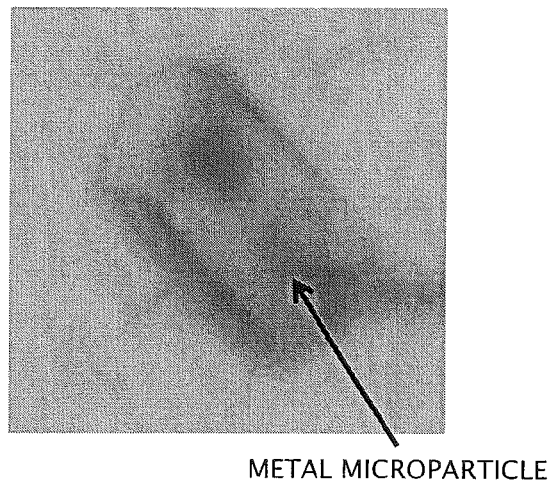

FIG. 32 is an enlarged view of a crystal portion from FIG. 31.

Figure 33:
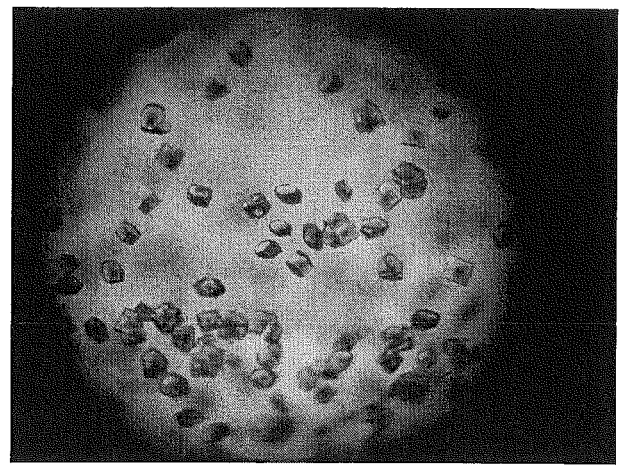

FIG. 33 is a diagram from an example of the present invention, illustrating a microscope photograph of lysozyme crystals obtained at a holding temperature of 4° C. using a crystallization solution having a lysozyme concentration of 1.05 mM, a NaCl concentration of 300 mM, a pH 8 buffer concentration of 100 mM, and also containing platinum microparticles.

Figure 34:
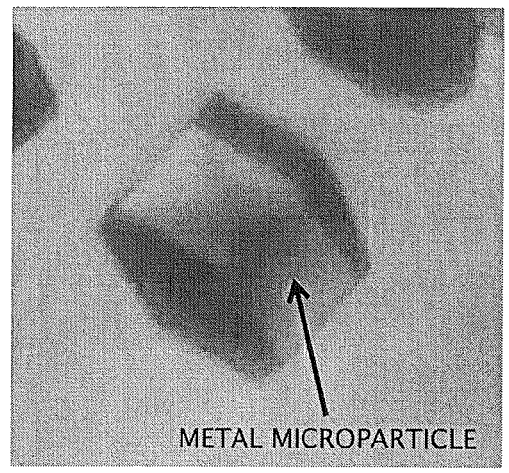

FIG. 34 is an enlarged view of a crystal portion from FIG. 33.

BEST MODE FOR CARRYING OUT THE INVENTION

Embodiments of the present invention are described below. These embodiments are merely examples of carrying out the present invention, and the present invention is in no way limited by these embodiments.

Protein crystals differ significantly from crystals of inorganic compounds and organic compounds in that approximately 50% or more of the crystal volume is occupied by water, with a multitude of water molecules required for retaining the structure of the protein. The inventors of the present invention have developed a method in which a nano-substance is incorporated within these spaces occupied by water (which vary in size depending on the type of protein, but are typically pores having a size of approximately 1 nm to approximately 100 nm), thereby achieving multidimensional accumulation of the nano-substance and obtaining an accumulated product of the nano-substance. In other words, a method according to an embodiment of the present invention is a nano-substance multidimensional accumulation method that uses a protein crystal as a template and causes self assembly of a nano-substance within the pores of the crystal, thereby achieving multidimensional accumulation of the nano-substance inside the crystal.

The method according to this embodiment of the present invention is a technique that enables an accumulated product of the nano-substance to be produced using a simple apparatus, at low cost, by a simple process that requires few conditions to be controlled and requires minimal energy and no complex items, and with good reproducibility. This method can be applied to nano-substances comprising all manner of materials and nano-substances having various particle sizes.

The method according to the embodiment of the present invention comprises crystallizing a protein in a state where the protein and the nano-substance co-exist within a solvent, thereby accumulating the nano-substance within the pores of the protein crystals to obtain an accumulated product of the nano-substance. Specifically, the method employs the following procedure, for example.

(1) A nano-substance that is stable under the protein crystallization conditions is prepared.

(2) The protein and the nano-substance are placed in a state of co-existence in an environment that represents the crystallization conditions.

(3) Using the protein crystals as a template, the nano-substance is incorporated within the pores of the crystals by a process of self-assembly, thereby growing crystals in which the nano-substance is accumulated multidimensionally inside the crystals.

The procedure described above is described below in further detail.

(1) A nano-substance that is stable under the protein crystallization conditions is prepared.

As described below, protein solubility regulators and the like are typically added to the crystallization solution, which often has a high salt concentration. Accordingly, a nano-substance such as a microparticle or biomolecule that can be stably dissolved or dispersed within a high salt concentration solution is preferably prepared. In the case of microparticles, examples include stabilized nano-substances such as stabilized microparticles that have been stabilized by a stabilizer, and specific examples include carboxylic acid-stabilized microparticles such as citric acid-stabilized microparticles and oxalic acid-stabilized microparticles, surfactant-stabilized microparticles such as sodium dodecyl sulfate (SDS)-stabilized microparticles and oleic acid-stabilized microparticles, and polymeric compound-stabilized microparticles such as polyvinylpyrrolidone (PVP)-stabilized microparticles and polyvinylpyridine-stabilized microparticles.

These stabilized nano-substances such as stabilized microparticles can be obtained by methods such as reduction methods and laser ablation methods.

There are no particular limitations on the nano-substance used in the present embodiment provided the substance has particles of a nano-order size, and examples include nano-size microparticles, biomolecules and soft matter. The term "nano-size" typically describes sizes of approximately 1 nm to approximately 1,000 nm.

Examples of the microparticles include metal microparticles, non-metal microparticles and polymer microparticles. As mentioned above, in order to obtain microparticles that are stable under the protein crystallization conditions, the surface of the microparticles may be stabilized using a stabilizer.

There are no particular limitations on the metal microparticles, provided the microparticles comprise a typical metal or transition metal, and specific examples of the metal include transition metals such as Ti, V, Cr, Mn, Fe, Co, Ni, Cu, Sc, Y, Zr, Nb, Mo, Tc, Hf, Ta, W, Au, Ag, Ru, Rh, Pd, Os, Ir, Pt, Re, the lanthanoids and the actinoids, as well as Zn, Cd, Hg, Al, Ga, In, Tl, Si, Ge, Sn, Pb, As, Sb and Bi. Among the transition metals, Au, Ag, Ru, Rh, Pd, Os, Ir, Pt, Cu, Fe, Ni, Co, Cr, Mn, Mo, W, Ta and Nb are preferred, the noble metals such as Au, Ag and the platinum group metals (Ru, Rh, Pd, Os, Ir and Pt) are more preferred due to factors such as their resistance to oxidation, and Au and Pt are particularly desirable. Further, microparticles of composite metals such as GaAs, GaTe and CdSe may also be used.

Examples of the non-metal microparticles include microparticles of organic compounds such as organic dyes and organic pigments, and inorganic compounds such as inorganic pigments.

Examples of the polymer microparticles include microparticles of polystyrene, polyethylene, polypropylene, and latex.

Examples of biomolecules that may be used as the nano-substance include membrane proteins, proteins, nucleic acids and protein-nucleic acid composites that are themselves difficult to crystallize.

Examples of soft matter that may be used as the nano-substance include emulsions and nano-gels.

There are no particular limitations on the method used for producing the metal microparticles, and examples include the SF-LAS method (surfactant-free laser ablation in solution) in which the surface of a metal plate is ablated by laser irradiation or microwave irradiation within a liquid such as water, the SC-LAS method (surfactant-controlled laser ablation in solution) in which the surface of a metal plate is ablated by laser irradiation or microwave irradiation within a liquid such as water containing an added surfactant, methods in which a chemical reduction is performed, and methods in which a discharge is performed in solution. Adding a surfactant or the like to the metal microparticles can stabilize the metal microparticles, which is preferred in terms of factors such as facilitating the operations during production.

Examples of surfactants that may be used include anionic, cationic, nonionic and amphoteric surfactants. For reasons including the solubility of the surfactant and the ability to stabilize the metal microparticles within a solvent, sodium dodecyl sulfate (SDS) is typically used.

The average particle size of the microparticles is typically not more than approximately 1,000 nm, as a high dispersibility of the microparticles within the crystallization solution is preferred, and is preferably within a range from approximately 1 nm to approximately 100 nm, and more preferably from approximately 5 nm to approximately 20 nm. If the average particle size of the microparticles is less than 1 nm, then the operations may become complicated. The average particle size of the microparticles can be measured, for example, using a light scattering measurement apparatus (model DLS-7000) manufactured by Otsuka Electronics Co., Ltd.

(2) The protein and the nano-substance are placed in a state of co-existence in an environment that represents the crystallization conditions.

The aforementioned nano-substances are placed in a state of co-existence within a solution of the protein under the crystallization conditions, thus preparing the crystallization solution. By adjusting the abundance ratio between the protein and the nano-substance, and the pH and the like of the crystallization solution, properties such as the amount of the nano-substance incorporated within the crystals can be controlled.

Examples of the protein that is crystallized to provide pores within the resulting crystals include lysozyme, bovine serum albumin (BSA) and amylase. In terms of ease of availability and ease of crystallization and the like, lysozyme and BSA are preferred.

There are no particular limitations on the solvent used for the crystallization, provided the solvent is capable of dissolving the protein and either dissolving or dispersing the nano-substance as uniformly as possible, and specific examples include water and typical organic solvents. There are no particular limitations on the water, examples of which include tap water, ground water, pure waters such as ion-exchanged water, and ultra pure water, but from the viewpoint of promoting the crystallization, a water containing minimal impurities is preferable, and a pure water such as ion-exchanged water or ultra pure water is usually used. Examples of organic solvents that may be used include alcohol-based solvents such as methanol, ethanol and isopropyl alcohol, aromatic solvents such as benzene and toluene, halogenated solvents such as methylene chloride, chloroform and carbon tetrachloride, linear saturated hydrocarbon solvents such as n-hexane and n-heptane, cyclic saturated hydrocarbon solvents such as cyclohexane, and acetonitrile and the like. Among these, water and alcohol-based solvents are preferred in terms of offering a wide range of application, and water is particularly preferred.

There are no particular limitations on the concentrations of the protein and the nano-substance within the crystallization solution, and these concentrations may be determined in accordance with factors such as the ease of crystallization of the protein, the ease of incorporation of the nano-substance within the crystal pores, the crystallization temperature, and the nature of the protein solubility regulator. The concentration of the protein within the crystallization solution is, for example, typically within a range from approximately 0.1 mM to approximately 100 mM, whereas the concentration of the nano-substance is, for example, typically within a range from approximately 1 pM to approximately 100 mM.

There are no particular limitations on the pH of the crystallization solution, although the shape of the protein crystals can be changed by altering the pH. This change of shape also may alter the region(s) in which the nano-substance is incorporated. For example, in those cases where lysozyme is used as the protein that provides the pores, when the pH is approximately 6 or lower, the {110} sector may enlarge, whereas when the pH is approximately 7 or higher, the {101} sector may enlarge. If metal microparticles are used as the nano-substance, then because the metal microparticles are incorporated within the {101} sector, the size of the region in which the nano-substance is incorporated may change depending on the pH.

In order to facilitate crystallization of the protein, a protein solubility regulator that regulates the solubility of the protein within the crystallization solution is preferably also included in the solution. Examples of the protein solubility regulator include inorganic salts such as sodium chloride and ammonium sulfate, alcohols such as polyethylene glycol (PEG) and ethanol, and nonionic surfactants such as NP40 (polyoxyethylene (9) octylphenyl ether).

There are no particular limitations on the concentration of the protein solubility regulator within the crystallization solution, which may be determined in accordance with factors such as the ease of crystallization of the protein being used, the concentration of the protein within the crystallization solution, and the crystallization temperature (holding temperature). For example, the concentration of the protein solubility regulator is typically within a range from approximately 1 mM to approximately 1,000 mM.

(3) Using the protein crystals as a template, the nano-substance is incorporated within the pores of the crystals by a process of self-assembly, thereby growing crystals in which the nano-substance is accumulated multidimensionally inside the crystals.

When crystallizing the protein, either a vapor diffusion method such as the hanging drop method or the sitting drop method, or a batch method or the like may be used. This may enable the nano-substance to be incorporated within the spaces (pores) occupied by water or the like within the protein crystals, thereby achieving multidimensional accumulation of the nano-substance within the crystal.

The hanging drop method is a method in which a liquid droplet of the crystallization solution comprising the protein and the nano-substance is adhered to and suspended from a cover glass or the like, and the liquid droplet is then subjected to vapor equilibration in a sealed system with a reservoir solution having a volume approximately 100 times that of the droplet.

The sitting drop method is a method in which a liquid droplet of the crystallization solution comprising the protein and the nano-substance is placed inside an indentation, and the liquid droplet is then subjected to vapor equilibration in a sealed system with a reservoir solution having a volume approximately 100 times that of the droplet.

For example, the reservoir solution is typically a solution containing the same composition as the crystallization solution excluding the protein and the nano-substance, or a solution equivalent to the final target composition.

The crystallization temperature may be determined in accordance with factors such as the ease of crystallization of the protein being used, the concentrations of the protein and the nano-substance within the crystallization solution, and the concentration of the protein solubility regulator. There are no particular limitations on the crystallization temperature, provided the protein and the nano-substance and the like being used do not decompose. For example, the temperature is typically within a range from approximately 0° C. to approximately 90° C.

There are no particular limitations on the time allowed for the crystallization, which may be determined in accordance with factors such as the ease of crystallization of the protein being used, the concentrations of the protein and the nano-substance within the crystallization solution, and the concentration of the protein solubility regulator. For example, the time is typically within a range from approximately 60 minutes to approximately 100 hours.

The accumulated product of a nano-substance obtained in the method for producing an accumulated product of a nano-substance according to the present embodiment may be used as a photonic material in a photonic device, or within a semiconductor device or the like.

As illustrated within the examples described below, in which metal microparticles of gold, silver or platinum are accumulated within the pores of protein crystals, the method according to the present embodiment is a technique that enables accumulation to be performed using the same process for different nano-substances comprising various materials. Further, the fact that accumulation of the microparticles is possible regardless of fluctuations in the particle sizes of the microparticles of gold, silver and platinum respectively indicates that, in the present method, there may be a considerably large degree of freedom in the particle size relative to the ability to achieve accumulation of the microparticles. Accordingly, the present method enables the accumulation technique to be applied to nano-substances comprising various materials and nano-substances of various sizes, which is necessary when attempting to control the physical properties of photonic materials and the like. Further, in the present method, the nano-substance is accumulated within protein crystals, and therefore even if the nano-substance such as the microparticles is formed of a substance having high density, precipitation of the nano-substance or secondary aggregation of particles of the nano-substance may be unlikely, and an accumulated product of the nano-substance that exhibits excellent dispersion stability of the nano-substance can be obtained. The fact that the permissible range of raw materials for the nano-substances and the permissible range for the particle size of those nano-substances are both large is a significant feature of the present invention.

Further, conventional accumulation techniques may require special techniques and/or energy input to control the accumulation, including gelling of microparticle solutions, electric field application, liquid film formation by flow casting of microparticle dispersions onto substrate surfaces, advection accumulation methods, accumulation by forced oscillation, or the use of self-assembled monolayers (SAM). The accumulation technique of the present method enables a three dimensional accumulated product of a nano-substance to be produced using a simple apparatus, at low cost, by a simple process that requires few conditions to be controlled and requires minimal energy and no complex items, and with good reproducibility, and it is thought that this method will lead to the development of novel devices comprising combinations of nano-substances and biopolymers.

The accumulated product of a nano-substance obtained using the method for producing an accumulated product of a nano-substance according to the present embodiment can also be used for analyzing the structure of the nano-substance.

Methods of analyzing the structures of nano-substances such as microparticles frequently employ TEM or SEM microscopes. However with these methods, obtaining information down to the atoms or molecules that constitute the nano-substance tends to be difficult. However, if the X-ray diffraction scattering image or the like of a "protein+nano-substance" crystal obtained using the present method is measured, then by subtracting the diffraction scattering image of the known "protein" from the diffraction scattering image of the "protein+nano-substance", the diffraction scattering image of the unknown "nano-substance" can be obtained, thus yielding a novel analysis method that enables information relating to the structure of the nano-substance to be obtained at a resolution equivalent to the atoms and molecules that constitute the nano-substance. In other words, by using an arbitrary analysis technique to obtain an analysis value for a "protein+nano-substance" crystal prepared using the present method, and then subtracting the analysis value for the known "protein", an analysis value for the unknown "nano-substance" can be obtained, meaning information relating to the structure of the nano-substance can be obtained.

There are no particular limitations on the analysis techniques that may be used for analyzing the structure of the nano-substance, and examples include X-ray diffraction, small angle X-ray scattering, and neutron scattering.

EXAMPLES

The present invention is described below in further detail using examples and comparative examples, but the present invention is in no way limited by the examples presented below.

Example 1

(1) Preparation of Gold Microparticles, Silver Microparticles and Platinum Microparticles Protein solubility regulators such as salts and PEG are added to crystallization solutions, with the solutions often having a high salt concentration. Accordingly, gold microparticles are investigated as an example of metal microparticles that can be dispersed even within solutions having a high salt concentration. Investigation of the dispersibility within high salt concentration solutions of gold microparticles containing no added stabilizer, citric acid-stabilized gold microparticles, SDS-stabilized gold microparticles, and PVP-stabilized gold microparticles and the like reveals that gold microparticles stabilized with PVP (viscosity coefficient K: 30) (hereinafter referred to as "PVP gold microparticles") exhibit the most superior dispersibility. In a method for synthesizing these PVP gold microparticles, first, 111 mg of PVP is dissolved in 10 mL of a 0.1 mM $HAuCl_4$ solution. To the resulting solution is added 0.1 mL of an $NaBH_4$ solution of concentration 0.1 mM, and the resulting mixture is stirred with a stirring bar for 12 hours at 25° C. Washing of the gold microparticles by precipitating the gold microparticles using a centrifuge and subsequently re-dispersing the microparticles in pure water is repeated three times. The resulting dispersion is then passed through a filter having a pore size of 0.45 μm, yielding PVP gold microparticles.

A similar procedure is used to prepare silver microparticles and platinum microparticles. With the exception of using $AgNO_3$ and $HPtCl_4$ instead of $HAuCl_4$, the synthesis method is the same as that described above for the gold microparticles.

(2) Crystallization of Simple Lysozyme

Using lysozyme as the protein to be crystallized, and using the simple lysozyme crystallization conditions listed below, the sitting drop method is used to perform crystal growth at different pH levels, and the precipitated state of the crystals is then inspected using a stereomicroscope (magnification: 100×) (FIGS. 1 to 8). The results reveal that the crystal system is tetragonal, and it is also evident that when the pH is 6 or lower, elongated crystals are formed due to the enlargement of the {001} sector, whereas when the pH is 7 or higher, rounded crystals are formed due to the enlargement of the {101} sector.
[Solution Composition]
 pH 3, 4, 5, 6, 7, 8, 9, 11 (50 mM)
 NaCl (300 mM)
 0.7 mM lysozyme
 solvent: ion-exchanged water
[Reservoir Solution Composition]
 pH 3, 4, 5, 6, 7, 8, 9, 11 (50 mM)
 NaCl (300 mM)
 solvent: ion-exchanged water
[Holding Temperature]
 4° C.

(3) Multidimensional Accumulation of Gold Microparticles Using Lysozyme

Based on the results of (2), PVP gold microparticles are added to a 1.05 mM supersaturated solution of lysozyme, the sitting drop method is used to hold the resulting dispersion under the conditions listed below, and the precipitated state of the crystals is then inspected using a stereomicroscope.
[Solution Composition]
 pH 3, 4, 5, 6, 7, 8, 9, 11 (50 mM)
 NaCl (300 mM)
 0.7 mM lysozyme
 solvent: ion-exchanged water
[Reservoir Solution Composition]
 pH 3, 4, 5, 6, 7, 8, 9, 11 (50 mM)
 NaCl (300 mM)
 solvent: ion-exchanged water
[Holding Temperature]
 4° C.

The results are illustrated in FIG. 9 to FIG. 24. The gold microparticles can be incorporated within the lysozyme crystals at all of the different pH levels. Further, it is evident that the gold microparticles can be incorporated within the {101} sector.

(4) Measurement of Ultraviolet-Visible Spectrum of Lysozyme Crystals Containing Multidimensionally Accumulated Gold Microparticles The lysozyme crystals containing the multidimensionally accumulated gold microparticles are washed twice with a lysozyme crystallization mother liquor containing no gold microparticles, and are then placed in an optical cell and subjected to an ultraviolet-visible spectral measurement (FIG. 25). The result reveals a surface plasmon resonance at 520 nm due to the gold microparticles. Further, the fact that no red shift in the surface plasmon resonance is observed confirms that the gold microparticles can be incorporated in a dispersed state within the lysozyme crystals.

(5) Multidimensional Accumulation of Silver Microparticles Using Lysozyme

Based on the results of (2), PVP silver microparticles are added to a 1.05 mM supersaturated solution of lysozyme, the sitting drop method is used to hold the resulting dispersion under the conditions listed below, and the precipitated state of the crystals is then inspected using a stereomicroscope.
[Solution Composition]
  pH 7, 8, 9 (50 mM)
  NaCl (300 mM)
  0.7 mM lysozyme
  solvent: ion-exchanged water
[Reservoir Solution Composition]
  pH 7, 8, 9 (50 mM)
  NaCl (300 mM)
  solvent: ion-exchanged water
[Holding Temperature]
  4° C.

The results are illustrated in FIG. 26 to FIG. 28. The silver microparticles can be incorporated within the lysozyme crystals at all of the different pH levels. Further, it is evident that, in a similar manner to the gold microparticles, the silver microparticles can be incorporated within the {101} sector.

(6) Multidimensional Accumulation of Platinum Microparticles Using Lysozyme

Based on the results of (2), PVP platinum microparticles are added to a 1.05 mM supersaturated solution of lysozyme, the sitting drop method is used to hold the resulting dispersion under the conditions listed below, and the precipitated state of the crystals is then inspected using a stereomicroscope.
[Solution Composition]
  pH 6, 7, 8 (50 mM)
  NaCl (300 mM)
  0.7 mM lysozyme
  solvent: ion-exchanged water
[Reservoir Solution Composition]
  pH 6, 7, 8 (50 mM)
  NaCl (300 mM)
  solvent: ion-exchanged water
[Holding Temperature]
  4° C.

The results are illustrated in FIG. 29 to FIG. 34. The platinum microparticles can be incorporated within the lysozyme crystals at all of the different pH levels. Further, it is evident that, in a similar manner to the gold microparticles, the platinum microparticles can be incorporated within the {101} sector.

In this manner, accumulated products of nano-substances can be produced at low cost, by a simple process that requires few conditions to be controlled and requires minimal energy, and with good reproducibility.

The invention claimed is:

1. A method of producing an accumulated product of particles of a nano-substance, the method comprising:
  providing stabilized particles of the nano-substance, wherein the particle size of the particle is not more than approximately 1000 nm;
  providing a solution comprising a protein and a solvent, wherein the protein provides pores within the resulting crystals when crystallized;
  mixing the stabilized particles with the solution to produce a dispersion of the stabilized particles in the solution; and
  crystallizing the protein present in the dispersion using a vapor diffusion or a batch method, thereby accumulating the particles within pores in crystals of the protein to obtain the accumulated product of the particles of nano-substance.

2. The method according to claim 1, wherein the solution further comprises a protein solubility regulator that regulates solubility of the protein present in the solvent.

3. The method according to claim 1, wherein
  the nano-substance is at least one of a metal and a biomolecule.

4. The method according to claim 1, wherein the step of crystalizing the protein comprises using a sitting drop method.

5. The method according to claim 1, wherein the stabilized micro-particles of the nano-substance are selected from the group consisting of carboxylic acid-stabilized micro-particles, surfactant-stabilized micro-particles, and a polymeric compound stabilized micro-particles.

6. The method according to claim 1, wherein the stabilized micro-particles of the nano-substance are selected from the group consisting of citric acids-stabilized micro-particles, oxalic acid-stabilized micro-particles, sodium dodecyl sulfate (SDS) stabilized micro-particles, oleic acid-stabilized micro-particles, polyvinylpyrrolidone (PVP)-stabilized micro-particles, and polyvinylpyridine-stabilized micro-particles.

7. The method according to claim 1, wherein the stabilized micro-particles are obtained by reduction method or laser ablation method.

8. The method according to claim 1, wherein the stabilized micro-particles comprise a metal selected from the group consisting of Ti, V, Cr, Mn, Fe, Co, Ni, Cu, Sc, Y, Zr, Nb, Mo, Tc, Hf, Ta, W, Au, Ag, Ru, Rh, Pd, Os, Ir, Pt, Re, Zn, Cd, Hg, Al, Ga, In, Tl, Si, Ge, Sn, Pb, As, Sb, Bi, Au, Ag, Ru, Rh, Pd, Os, Ir, Pt, Cu, Fe, Ni, Co, Cr, Mn, Mo, W, Ta, Nb, Au, Ag, Ru, Rh, Pd, Os, Ir, and Pt.

9. The method according to claim 1, wherein the stabilized micro-particles comprise a composite metal selected from the group consisting of GaAs, GaTe, and CdSe.

10. The method according to claim 1, wherein the stabilized micro-particles comprise a polymer selected from the group consisting of polystyrene, polyethylene, polypropylene, and latex.

11. The method according to claim 1, wherein the stabilized micro-particles comprise PVP-stabilized gold microparticles.

12. The method according to claim 1, wherein the stabilized micro-particles comprise PVP-stabilized silver microparticles.

13. The method according to claim 1, wherein the stabilized micro-particles comprise PVP-stabilized platinum micro-particles.

14. The method according to claim 1, wherein the protein is selected from the group consisting of lysozyme, bovine serum albumin (BSA), and amylase.

15. The method according to claim 1, wherein the protein is lysozyme.

16. The method according to claim 1, wherein the vapor diffusion method is a hanging drop method or a sitting drop method.

* * * * *